(12) United States Patent
Baldauf et al.

(10) Patent No.: US 7,722,943 B2
(45) Date of Patent: May 25, 2010

(54) FASTENER STRIPS FOR DIAPERS

(75) Inventors: Georg Baldauf, Laer (DE); Marcus Schönbeck, Versmold (DE)

(73) Assignee: Nordenia Deutschland Gronau GmbH, Gronau (DE)

( * ) Notice: Subject to any disclaimer, the term of this patent is extended or adjusted under 35 U.S.C. 154(b) by 509 days.

(21) Appl. No.: 11/402,075

(22) Filed: Apr. 11, 2006

(65) Prior Publication Data

US 2006/0247567 A1    Nov. 2, 2006

(30) Foreign Application Priority Data

Apr. 12, 2005    (DE) .................. 10 2005 016 895

(51) Int. Cl.
*B32B 27/12* (2006.01)
*B32B 3/06* (2006.01)
*D04H 1/00* (2006.01)
*D04H 3/00* (2006.01)

(52) U.S. Cl. .................. 428/100; 428/99; 442/328; 442/329; 442/364; 442/394; 442/398

(58) Field of Classification Search .................. 428/100, 428/99; 442/328, 329, 364, 394, 398
See application file for complete search history.

(56) References Cited

U.S. PATENT DOCUMENTS

| | | | |
|---|---|---|---|
| 5,807,371 A * | 9/1998 | Toyoda et al. | 604/385.29 |
| 5,916,207 A * | 6/1999 | Toyoda et al. | 604/391 |
| 6,740,071 B2 | 5/2004 | Gibbs | |
| 2001/0039406 A1 * | 11/2001 | Hamajima et al. | 604/367 |
| 2003/0009144 A1 * | 1/2003 | Tanzer et al. | 604/391 |
| 2004/0249357 A1 | 12/2004 | Michielsen et al. | |
| 2005/0106980 A1 * | 5/2005 | Abed et al. | 442/395 |

FOREIGN PATENT DOCUMENTS

EP    0809 992 B1    12/1997
WO    WO 03/076179    9/2003

* cited by examiner

*Primary Examiner*—Brent T O'Hern
(74) *Attorney, Agent, or Firm*—Collard & Roe, P.C.

(57) ABSTRACT

A fastener strip for diapers has a center part that is elastic in the longitudinal direction of the strip when the fastener strip is pulled, a non-elastic end part to which a hook element is attached, and a non-elastic connector part for attachment to a diaper. The end part and the connector part are attached to the center part. The center part has a layer of an elastic spun-bonded non-woven fabric, which possesses preferred stretching properties in the longitudinal direction of the strip. The spun-bonded non-woven fabric is made of filaments that have a filament core of a thermoplastic elastomer and a filament mantle of a non-elastic thermoplastic polymer, stretched by means of stretching the spun-bonded non-woven fabric.

10 Claims, 4 Drawing Sheets

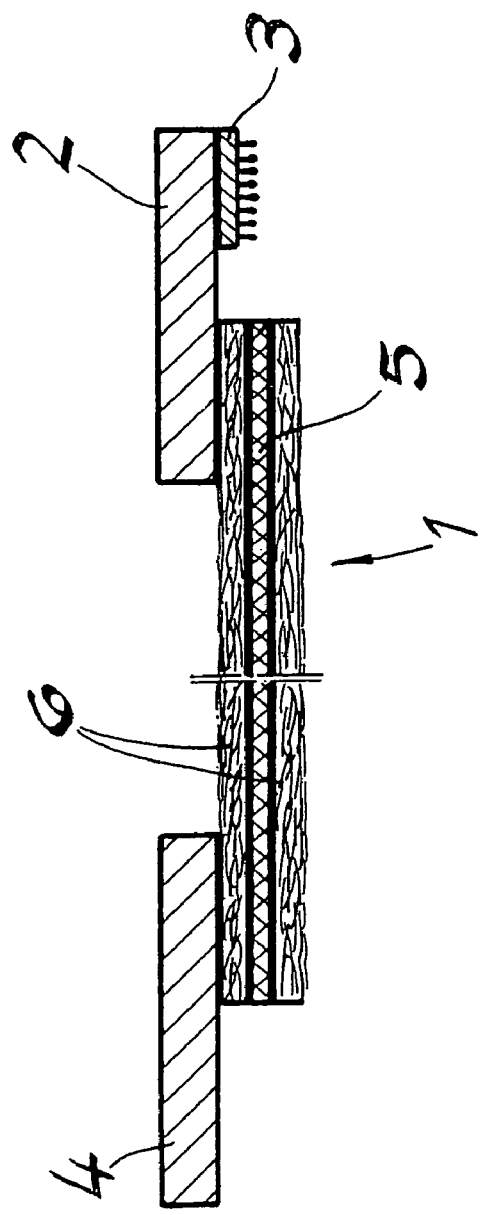
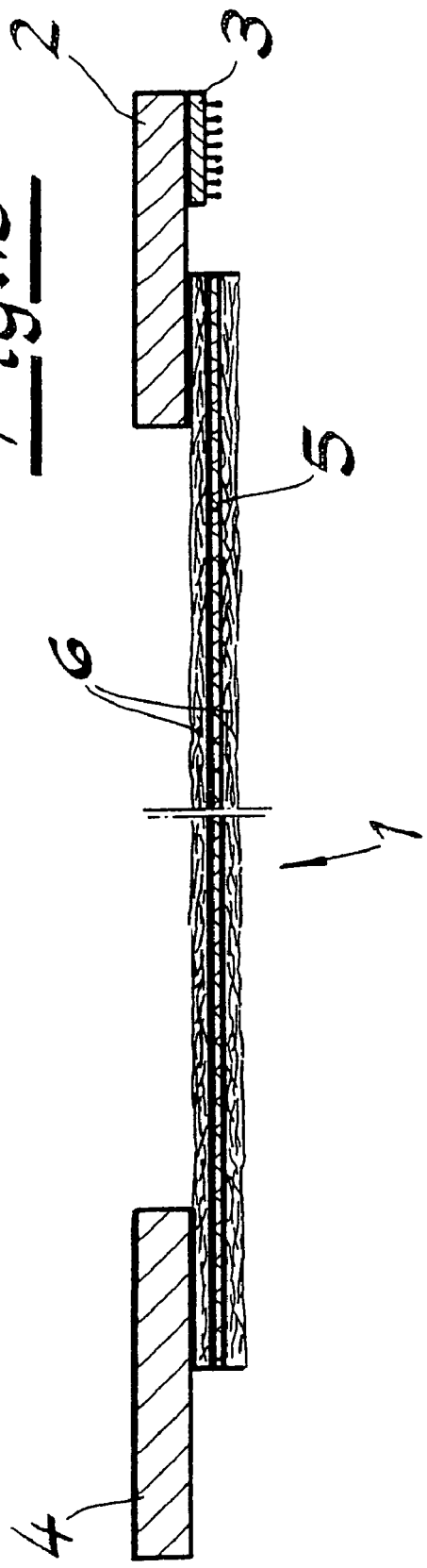

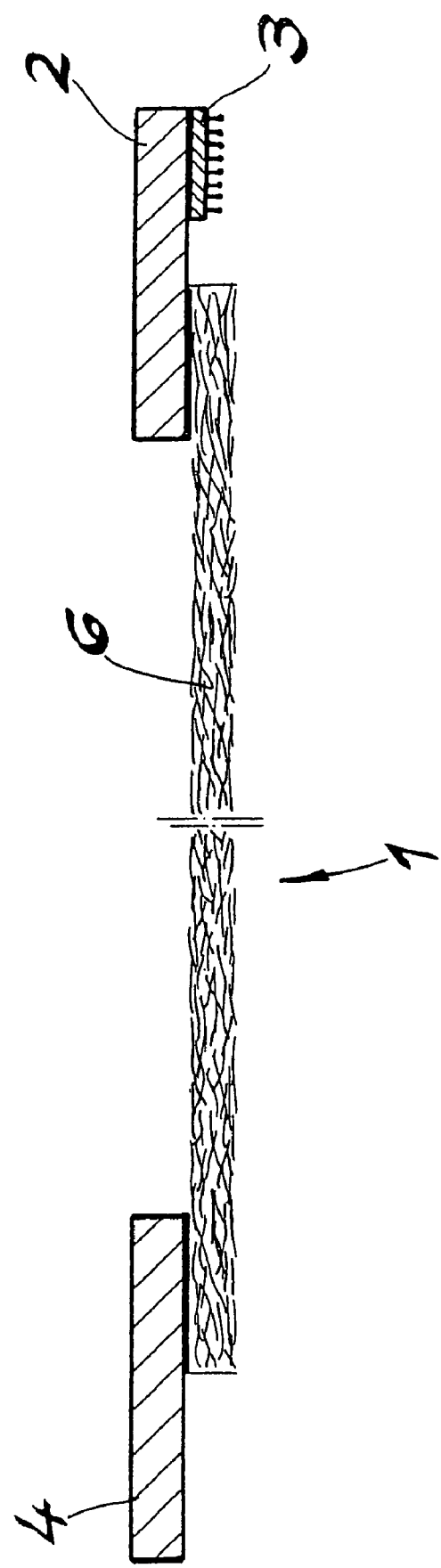

FASTENER STRIPS FOR DIAPERS

CROSS REFERENCE TO RELATED APPLICATIONS

Applicants claim priority under 35 U.S.C. §119 of German Application No. 10 2005 016 895.7 filed Apr. 12, 2005.

BACKGROUND OF THE INVENTION

1. Field of the Invention

The present invention relates to a fastener strip for diapers. More specifically, the fastener strip has a first center part that is elastic in the longitudinal direction of the strip when the fastener strip is pulled, a non-elastic end part having a hook element, and a non-elastic connector part for attachment to a diaper. The end part and the connector part are attached to the center part. The longitudinal direction of the strip extends from the connector part to the end part. The fastener strip is part of a mechanical hook-and-loop fastener on a diaper. One part of the hook-and-loop fastener is provided with female fastener elements and glued on in the front waistline region of the diaper. The related hook element is affixed to the fastener strip described, which is attached to the back waistline region of the diaper.

2. The Prior Art

A fastener strip for diapers, having the described characteristics, is known from EP 0 809 992 B1. The center part of the fastener strip consists of a plastically deformable film, onto which straight strips or strips disposed in spiral shape, made of an elastomer material, are applied. Before first-time use, the fastener strip does not demonstrate any elasticity. The fastener strip becomes elastic when it is stretched in the longitudinal direction of the strip during first-time use. In this connection, there is the risk that when the diaper fastener is closed, or as the diaper is worn, the elastic fastener strips are over-stretched. The over-stretching is connected with a permanent elongation of the material and has a negative effect on the fit of the diaper.

SUMMARY OF THE INVENTION

In view of this background, it is an object of the invention to provide a fastener strip for diapers, in which over-stretching due to improper use or due to stresses during use as intended is precluded, to a great extent.

Proceeding from a fastener strip having the characteristics described initially, these and other objects are achieved, according to the invention, by providing the center part with a layer of an elastic spun-bonded non-woven fabric that possesses preferred stretching properties in the longitudinal direction of the strip. The spun-bonded non-woven fabric is made of filaments that have a filament core of a thermoplastic elastomer and a filament mantle of a non-elastic thermoplastic polymer stretched by means of stretching the spun-bonded non-woven fabric.

The fastener strip according to the invention has a clearly perceptible elongation limit. The center part of the fastener strip can be stretched to this limit with little force. When the stress is relieved, the center part returns elastically to its original status. When the fastener strip is used as a diaper fastener tab, this range is perceived as an elastic working range. When the elongation limit determined by the material is reached, a great increase in the force required for further stretching is noticed, and the diaper fastener behaves non-elastically above the defined elongation limit. The properties of the fastener strip according to the invention also have an advantageous effect on the fit of the diaper. Because of the elasticity of the diaper fastener tab, i.e. of the fastener strip, the diaper fastener can be stretched, and relaxed again, in accordance with the movements of the person. In this connection, the diaper fastener is not over-stretched, because of the existing elongation limit, so that the fit of the diaper is maintained during use. The percentage elongation of the center part until the elongation limit is reached is determined by the pre-stretching of the non-elastic filament components of the spun-bonded non-woven fabric.

The filaments of the spun-bonded non-woven fabric are structured as so-called bicomponent fibers. Suitable polymer mixtures for the elastomer filament core comprise, for example, polyurethanes, styrene block copolymers, polyethylenes, polyethylene copolymers, and polypropylene copolymers, as well as mixtures of these polymers, as the elastic component. The non-elastic filament mantle can be made for example, of polypropylene or polyethylene. The spun-bonded non-woven fabric is produced from endless filaments that are drawn off from spinning jets by means of an air stream, utilizing a Venturi effect, and laid down onto a spinning band in a tangled position.

The fiber non-woven fabric is compacted. The compacting takes place by means of a calender, under the influence of heat and pressure, by means of needling, hot-air compacting, or other methods for compacting of non-woven fabrics that are known to a person skilled in the art. Subsequent stretching of the compacted fiber non-woven fabric in a direction that corresponds to the longitudinal direction of the strip results in cold-stretching of the non-elastic filament components. The layer of the mantle polymer is oriented in the filament direction, whereby the mantle polymer, part of which has been oriented all the way to the tear limit, ensures a steep increase in the tear force values of the non-elastic film components. After stretching, the fiber non-woven fabric returns elastically to its original position, under the effect of the elastic core of the bicomponent fibers. By means of the aforementioned pre-stretching, an elastic spun-bonded non-woven fabric having a defined elongation limit is produced, which can be elastically stretched up to a clearly perceivable elongation limit, in accordance with the degree of pre-stretching.

The center part, as a single-layer element, can consist exclusively of a spun-bonded non-woven fabric, whereby the spun-bonded non-woven fabric preferably has a weight per area unit between 80 g/m$^2$ and 200 g/m$^2$.

In another embodiment, the center part has an elastic carrier film onto which the spun-bonded non-woven fabric is laminated on one or both sides. The carrier film also possesses preferred stretching properties in the longitudinal direction of the strip. The elasticity of the center part, which determines the required force for stretching, i.e. the elastic return force, is co-determined by the properties of the carrier film. The spun-bonded non-woven fabric laminated onto the carrier film therefore preferably has a weight per area unit of only 10 to 25 g/m$^2$.

The carrier film is preferably a film made from a thermoplastic elastomer produced according to the film-casting or film-blowing method. Polymer mixtures suitable for this purpose include polyurethanes, styrene block copolymers, polyethylenes, polyethylene copolymers, polypropylene copolymers, and mixtures of these polymers as the elastic component. As a result of the orientation of the polymers during the extrusion process, the carrier film has a preferred stretching direction in one direction, and it is stiff and non-elastic in the transverse direction to that stretching direction. The carrier film can also contain cross-linked elastomers, such as nitrile-butadiene rubber (NBR) or ethylene-propylene-diene copolymer rubber (EPDM), for example.

The elastic carrier film of the center part preferably has a weight per area unit between 5 g/m² and 150 g/m². It is a monofilm of a thermoplastic elastomer. Alternatively, the elastic carrier film consists of a multi-layer coextrusion film that has a core of a thermoplastic elastomer and an adhesion-imparting layer disposed on one or both sides, to improve the adhesion of the adjacent spun-bonded non-woven fabric. It is practical if the adhesion-imparting layer has a high affinity for lamination glues. The thickness of the coextrusion film amounts to 50 μm to 150 μm, with a thickness ratio, in the case of a three-layer structure, of 1:10:1 to 1:30:1. The elastic core of the coextrusion film is always many times greater than the co-extruded adhesion-imparting layers. All of the layers of the coextrusion film can be made of elastic thermoplastic polymers. The adhesion-imparting layer can be modified by means of additives, so that the carrier film does not interlock and has a particularly good affinity to lamination glues. Mineral fillers as well as mixtures of styrene-isoprene-styrene block copolymer (SIS), styrene-butadiene-styrene block copolymer (SBS), styrene-ethylene butylene-styrene block copolymer (SEBS), and polyurethane (PU) polymers with polyolefins, such as polyethylene, polypropylene, ethylene vinyl acetate (EVA), and ethylene-propylene rubber (EPR), can be used as materials for the layers of the coextrusion film. The adhesion-imparting layer can furthermore be made of a polyolefin material.

The carrier film and the spun-bonded non-woven fabric of the center part are preferably bonded by means of an elastic hot-melt glue, whereby the glue application takes place in the form of dots, in grid-like manner, in the form of lines in stripes that run transverse to the stretching direction, or over the full area. The hot-melt glues used are preferably elastic thermoplastics on the basis of SIS, SBS or SEBS polymers, or mixtures of them. The hot-melt glue is preferably applied at weights per area unit between 2 g/m² and 20 g/m², between the elastic carrier film and the spun-bonded non-woven fabric. If the hot-melt glue is applied in lines, the distance between the lines of glue can amount to 0.2 mm to 5 mm, preferably 0.5 mm to 2 mm. The width of the glue track is 0.3 mm to 2 mm, for example, particularly preferably 0.5 mm to 1.5 mm.

For all the embodiments described above, the non-elastic filament component within the spun-bonded non-woven fabric is up to 60 wt.-%, preferably about 20 wt.-%, with reference to the material of the spun-bonded non-woven fabric, in each instance.

The non-elastic end parts and connector parts of the fastener strip, according to a preferred embodiment of the invention, are made of a non-woven fabric of polyolefin fibers, particularly of polypropylene fibers. It is practical to connect the end and connector parts with the center part by gluing and/or bonding. In a particularly advantageous embodiment, the end parts and connector parts are glued to the center part, and in addition, point-bonded, preferably by ultrasound.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views:

FIGS. 1a and 1b show a fastener strip according to the invention, in the non-stretched and the stretched state, respectively;

FIG. 2 shows another embodiment of the fastener strip;

DETAILED DESCRIPTION OF PREFERRED EMBODIMENTS

Referring now in detail to the drawings, FIGS. 1a and 1b show a fastener strip for an elastic diaper fastener. The fastener strip is made of a center part 1, which is elastic when the fastener strip is pulled in the longitudinal direction of the strip, a non-elastic end part 2 having a hook element 3, and a non-elastic connector part 4 for attachment to a diaper. End part 2 and connector part 4 are attached to center part 1. The longitudinal direction of the strip extends from connector part 4 to end part 2.

Figure 3B:
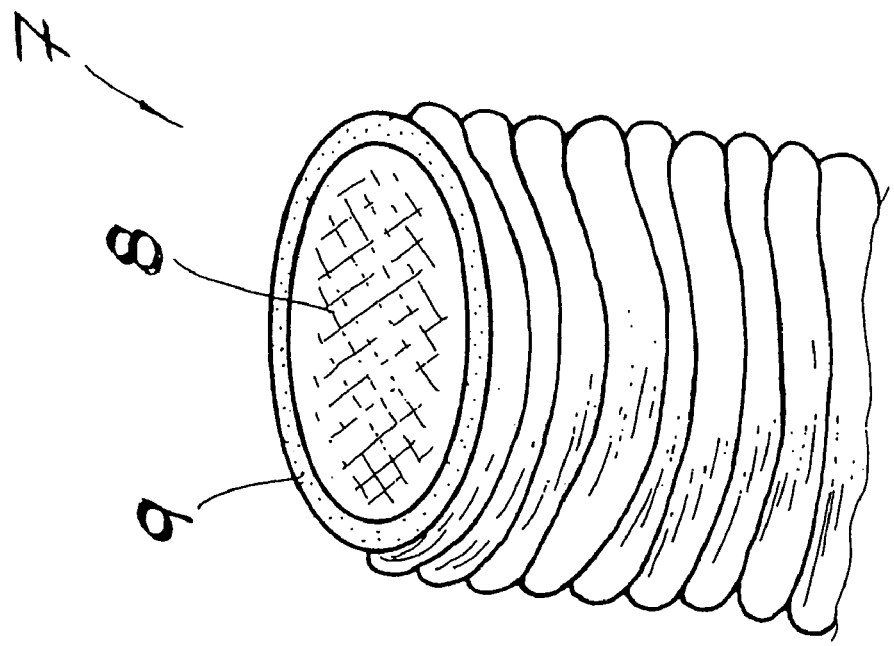
FIGS. 3a and 3b show a filament from which the spun-bonded non-woven fabric of the elastic center part of the fastener strip is produced.

In the exemplary embodiment shown in FIGS. 1a and 1b, center part 1 of the fastener strip is made of an elastic carrier film 5 and at least one layer of an elastic spun-bonded non-woven fabric 6 laminated on the film. Like spun-bonded non-woven fabric 6, carrier film 5 has preferred stretching properties in the longitudinal direction of the strip. Spun-bonded non-woven fabric 6, which is laminated onto carrier film 5, is made up of filaments 7. As shown in FIG. 3b, filaments 7 have a filament core 8 of a thermoplastic elastomer and a filament mantle 9 of a non-elastic thermoplastic polymer, stretched by means of elongation of the spun-bonded non-woven fabric. The weight per area unit of spun-bonded non-woven fabric 6 laminated onto the carrier film is preferably 10 g/m² to 25 g/m².

Figure 4:
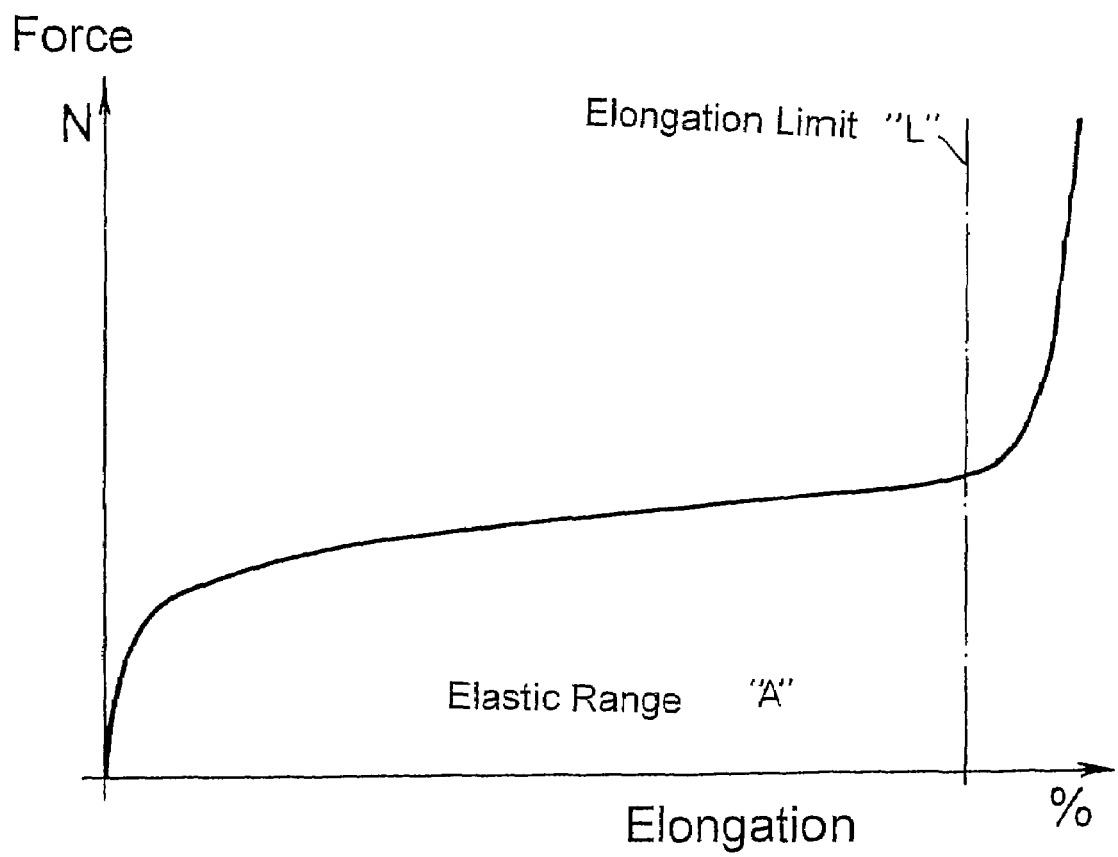
FIG. 4 is a strain/stress diagram of the fastener strip.

Hook element 3 disposed on non-elastic end part 2 has male fastener elements that form a hook-and-loop closure with female fastener elements. The female fastener elements are attached in the front waistline region of a diaper, not shown. A comparison of FIG. 1a with FIG. 1b shows that center part 1 of the fastener strip can be elastically stretched in the preferred elongation direction shown. The material of center part 1 permits elastic elongation by 30% to 150% of the original length, for example. Reaching the elastic elongation limit is defined by way of a steep increase in force. The elongation behavior of the material is shown in FIG. 4. In FIG. 4, the tensile force required for elongation is plotted above the elongation (elongation with reference to the original length). It is evident from FIG. 4 that center part 1 of the fastener strip can be stretched with little force up to the elongation limit. Over this elongation range, the center part elastically returns to its original position when the force is released. When the elongation limit established in the material has been reached, a great increase in force is required for further elongation. This range is clearly perceived as a non-elastic range.

In the exemplary embodiment of FIG. 2, center part 1 is a single-layer element and consists exclusively of an elastic spun-bonded non-woven fabric 6 that has a weight per area unit between 80 g/m² and 200 g/m². The elongation behavior of the material qualitatively corresponds to FIG. 3. It can be elastically stretched, with little force, up to an elongation limit that is defined by a steep increase in force, and is clearly perceived as a non-elastic range in the handling of the strip.

Elastic spun-bonded non-woven fabric 6 consists of filaments 7 that have a filament core 8 of a thermoplastic elastomer and a filament mantle 9 of a non-elastic thermoplastic polymer. Spun-bonded non-woven fabric 6 is modified by means of pre-stretching, causing the structure of the filaments to change.

Figure 3A:
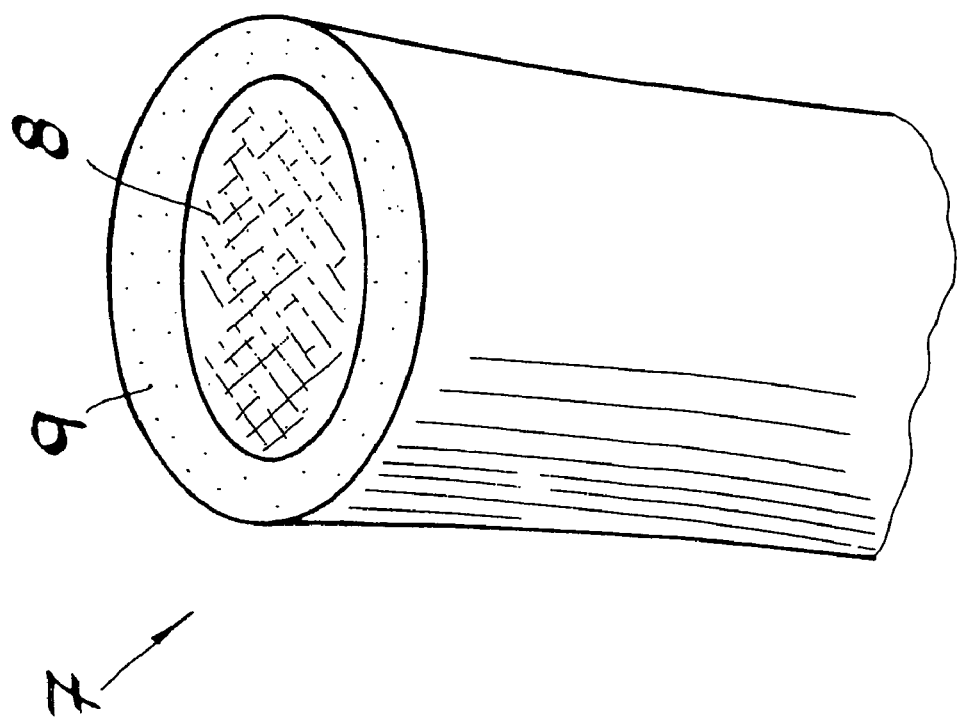

This change in structure becomes clear from a comparison of FIG. 3a with FIG. 3b. Before stretching, filaments 7 of the spun-bonded non-woven fabric have the geometry shown in FIG. 3a. By means of pre-stretching of the spun-bonded non-woven fabric, filament mantle 9 of the filaments is plastically deformed, while filament core 8 merely undergoes a reversible elastic deformation. After pre-stretching, filament 7 contracts again, and then possesses the contour shown in FIG. 3b. Because of the plastic deformation of non-elastic filament mantle 9, mantle 9 now has a corrugated structure. If filament 7 is stretched during use, non-elastic filament mantle 9 first aligns itself along elastic filament core 8 and offers practically no resistance to stretching.

When filament 7 reaches a non-corrugated contour again because of the stretching, which fundamentally corresponds to the representation in FIG. 3a, the elastic elongation limit of the fiber non-woven fabric has been reached. Elongation beyond this elongation limit can take place only if filament mantle 9 undergoes further cold-stretching. This second cold-stretching is connected with a steep increase in the force required for further elongation. In this range, the spun-bonded non-woven fabric therefore no longer has any elastic properties.

This absence of elastic properties becomes particularly clear from FIG. 4, in which the tensile force required for stretching a fastener strip according to the invention is plotted above the elongation. In the non-stretched state, filaments 7 of the center part have the contour shown in FIG. 3b. In the elastic stretching range "A," the curve runs relatively flat over a great range, so that only comparatively low forces are required to stretch the material in this range. When the upper limit of the elastic range has been reached, filaments 7 possess a contour that they also possessed during maximal stretching, during pre-stretching. In case of elongation beyond the elastic elongation limit "L," the force required for this elongation increases steeply upward, accompanied by further cold-stretching of non-elastic filament mantle 9. Therefore the size of elastic range "A" can be adjusted in targeted manner by means of the pre-stretching of filaments 7.

The non-elastic end and connector parts 2, 4 of the fastener strip consist of a non-woven fabric of polyolefin fibers, preferably of polypropylene fibers. End part 2 and connector part 4 have been glued onto center part 1 of the fastener strip, and additionally bonded to center part 1 by means of point bonds, preferably by means of ultrasound.

Although only a few embodiments of the present invention have been shown and described, it is to be understood that many changes and modifications may be made thereunto without departing from the spirit and scope of the invention as defined in the appended claims.

What is claimed is:

1. A fastener strip for diapers comprising:
    (a) a center part elastic in a longitudinal direction of the fastener strip when the fastener strip is pulled;
    (b) a non-elastic end part having a hook element; and
    c) a non-elastic connector part for attachment to a diaper;
    wherein said end part and said connector part are attached to said center part and the longitudinal direction of the fastener strip extends from said connector part to said end part;
    wherein said center part has a layer of an elastic spun-bonded non-woven fabric having selected stretching properties in the longitudinal direction of the fastener strip;
    wherein the spun-bonded non-woven fabric comprises filaments having a filament core of a thermoplastic elastomer and a filament mantle of a non-elastic thermoplastic polymer stretched by pre-stretching the spun-bonded nonwoven fabric in a stretching direction which corresponds to the longitudinal direction of the fastener strip;
    wherein said non-elastic filament components are cold-stretched as a result of said pre-stretching;
    wherein the center part comprises an elastic carrier film having first and second sides, the spun-bonded non-woven fabric being laminated onto one or both of said first and second sides;
    wherein said pre-stretching determines an elongation limit;
    wherein said center part can be stretched to said elongation limit and, when stress is relieved, returns elastically to its original status; and
    wherein when the clearly perceptible elongation limit is reached, a great increase in the force required for further stretching is noticed.

2. The fastener strip according to claim 1, wherein the spun-bonded non-woven fabric laminated onto the carrier film has a weight per area unit of 10 g/m$^2$ to 25 g/m$^2$.

3. The fastener strip according to claim 1, wherein the carrier film is a monofilm of a thermoplastic elastomer, or comprises a multi-layer coextrusion film that has a core of a thermoplastic elastomer and an adhesion-imparting layer disposed on one or both sides of the core to improve adhesion to the core of the spun-bonded non-woven fabric adjacent to the adhesion-imparting layer.

4. The fastener strip according to claim 1, wherein the carrier film and the spun-bonded non-woven fabric are bonded by means of an elastic hot-melt glue applied as dots, in a grid, in lines in stripes running transverse to the stretching direction, or over an entire area between the carrier film and the spun-bonded non-woven fabric.

5. The fastener strip according to claim 1, wherein the elastic carrier film has a weight per area unit between 5 g/m$^2$ and 150 g/m$^2$.

6. The fastener strip according to claim 1, wherein the spun-bonded non-woven fabric has up to 60 wt.-% non-elastic thermoplastic polymer.

7. The fastener strip according to claim 6, wherein the spun-bonded non-woven fabric has about 20 wt.-% non-elastic thermoplastic polymer.

8. The fastener strip according to claim 1, wherein the non-elastic end part and the connector part comprise a non-woven fabric of polyolefin fibers.

9. The fastener strip according to claim 8, wherein the polyolefin fibers are polypropylene fibers.

10. The fastener strip according to claim 1, wherein the end part and the connector part are connected with the center part by means of gluing or bonding.

* * * * *